US008682006B1

(12) United States Patent
Laroche et al.

(10) Patent No.: US 8,682,006 B1
(45) Date of Patent: Mar. 25, 2014

(54) NOISE SUPPRESSION BASED ON NULL COHERENCE

(75) Inventors: Jean Laroche, Santa Cruz, CA (US); Carlos Avendano, Campbell, CA (US)

(73) Assignee: Audience, Inc., Mountain View, CA (US)

( * ) Notice: Subject to any disclaimer, the term of this patent is extended or adjusted under 35 U.S.C. 154(b) by 390 days.

(21) Appl. No.: 13/157,238

(22) Filed: Jun. 9, 2011

Related U.S. Application Data

(60) Provisional application No. 61/405,122, filed on Oct. 20, 2010.

(51) Int. Cl.
*H04B 15/00* (2006.01)
*A61F 11/06* (2006.01)
*G10L 21/00* (2013.01)

(52) U.S. Cl.
USPC .......................... 381/94.1; 381/71.1; 704/226

(58) Field of Classification Search
USPC ...................................... 381/94.1–94.9, 71.1
See application file for complete search history.

(56) References Cited

U.S. PATENT DOCUMENTS

| | | | | |
|---|---|---|---|---|
| 8,223,988 | B2 * | 7/2012 | Wang et al. | 381/92 |
| 2007/0154031 | A1 | 7/2007 | Avendano et al. | |
| 2009/0323982 | A1 | 12/2009 | Solbach et al. | |
| 2011/0182436 | A1 | 7/2011 | Murgia et al. | |
| 2012/0027218 | A1 | 2/2012 | Every et al. | |

* cited by examiner

*Primary Examiner* — Vivian Chin
*Assistant Examiner* — Ammar Hamid
(74) *Attorney, Agent, or Firm* — Carr & Ferrell LLP

(57) ABSTRACT

Noise suppression is performed based on null coherence between sub-band signals of a primary acoustic signal and a secondary acoustic signal. The null coherence of a signal refers to portions of the signal that have high coherence and can be nullified by a null processor. The nullified component corresponds to target sources, such as an individual speaking into a phone. The coherence values indicate the presence of a target source and are used to suppress noise in portions of a signal that are not dominated by a desired target source. The inter-microphone level difference may be used in combination with the null coherence to provide noise suppression.

18 Claims, 7 Drawing Sheets

NOISE SUPPRESSION BASED ON NULL COHERENCE

CROSS-REFERENCE TO RELATED APPLICATIONS

This application claims the benefit of U.S. Provisional Application Ser. No. 61/405,122, filed Oct. 20, 2010, the disclosure of which is incorporated herein by reference.

BACKGROUND OF THE INVENTION

1. Field of the Invention

The present invention relates generally to audio processing, and more particularly, to a noise suppression processing of an audio signal.

2. Description of Related Art

There are numerous methods for reducing background noise in an adverse audio environment. A stationary noise suppression system suppresses stationary noise by either a fixed or varying amount. A fixed suppression system suppresses stationary or non-stationary noise by a fixed number of dB. The shortcoming of the stationary noise suppressor is that non-stationary noise will not be suppressed, whereas the shortcoming of the fixed suppression system is that it must suppress noise by a conservative level in order to avoid speech distortion at low signal-to-noise ratio (SNR).

Multiple microphone noise suppression algorithms can use an inter-microphone level difference (ILD) cue as a basis for discriminating between the background noise and the target speaker. While ILD is a very strong cue in many situations (especially in close-talk, with spread microphones), it is much less discriminative in others. For example, in far talk mode and for close microphones, the speech and noise ILD overlap to a large extent. Furthermore, even in close-talk mode, problems arise in "off-position" (when the phone is not in the ideal position for which it was calibrated). For these reasons, an ILD-only speech and noise discrimination is not optimal in all situations.

To overcome the shortcomings of the prior art, there is a need for an improved noise suppression system for processing audio signals.

SUMMARY OF THE INVENTION

The present technology provides noise suppression based on null coherence. The null coherence of a signal refers to portions of the signal that have high coherence and can be nullified by a null processor. The nullified component corresponds to the target source, such as an individual speaking into a phone. The coherence values indicate the presence of a target source and can be used to suppress noise in portions of a signal that are not dominated by a desired target source. The inter-microphone level difference may be used in combination with null coherence to provide noise suppression.

An embodiment includes a method for reducing noise within an acoustic signal. The method begins with receiving a first acoustic signal and a second acoustic signal. An energy level of a noise component in the first acoustic signal may be determined based on coherence between the first and second acoustic signals. A signal modification can then be applied to the first acoustic signal to reduce the energy level of the noise component, the signal modification based on the determined energy level of the noise component.

A system for performing noise reduction may include a memory, frequency analysis module, null coherence module, a modifier module, and a reconstructor module. The frequency analysis module may be stored in the memory and executed by a processor to generate sub-band signals in a cochlea domain from a primary time domain acoustic signal and secondary time domain acoustic signal. The null coherence module may be stored in the memory and executed by a processor to determine a null coherence between the sub-band signals. The modifier module may be stored in the memory and executed by a processor to modify a noise component based on the null coherence. The reconstructor module may be stored in the memory and executed by a processor to reconstruct a modified time domain signal from the modified sub-band signals provided by the modifier module.

DETAILED DESCRIPTION OF THE INVENTION

The present technology provides noise suppression based on null coherence. The null coherence of a signal identifies portions of the signal that have both a spatial null in a desired direction and a high coherence. The spatially nullified component corresponds to the direction of a target source, such as the direction of an individual speaking into a phone. The coherence values indicate the presence of a target source and can be used to suppress noise in portions of a signal that are not dominated by a desired target source. The present technology utilizes the spatial null and the coherence values, collectively referred to as null coherence herein, to remove noise in a received acoustic signal. Null coherence involves both null processing and coherence. This two part feature differs from prior audio processing systems that may only utilize a null feature.

Noise suppression based on null coherence is performed on acoustic signals received through two or more microphones. A frequency analysis may be performed on the acoustic signals to generate cochlea domain sub-band signals. A null coherence may be generated for each of the sub-bands. The null coherence may be determined from a ratio of energy levels between one or both of the microphone signals and a target-nullifying complex coefficient. A high coherence may correspond to a target source such as speech while a low null coherence value may correspond with noise and other non-target sources. A noise reduction mask is generated for each sub-band based at least in part on the null coherence and applied to the sub-band signal. An inter-microphone level difference and SNR may supplement the coherence in determining a level of noise suppression to apply to a sub-band.

Figure 1:
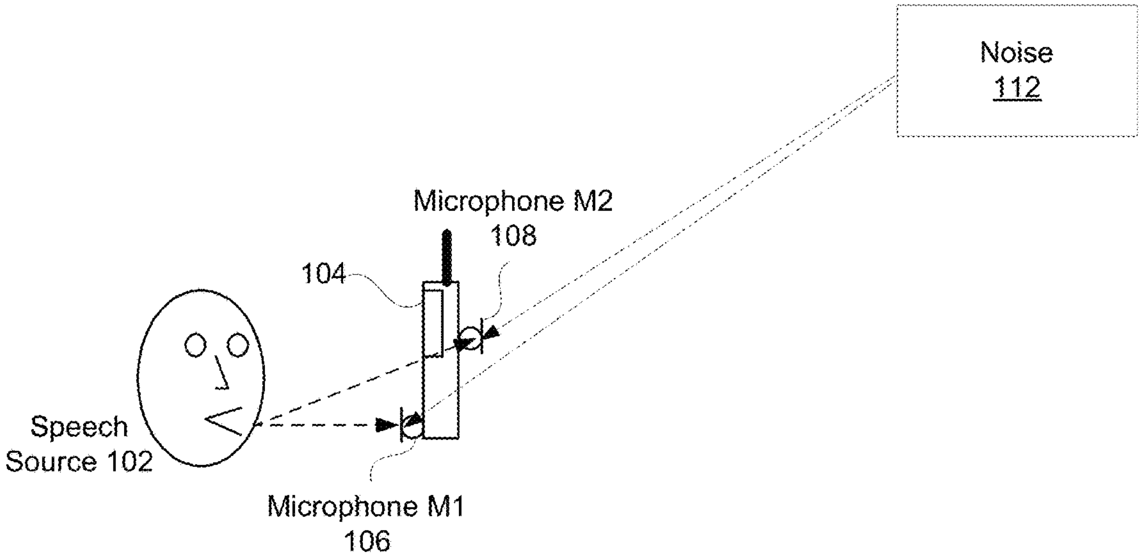
FIG. 1 is an illustration of an environment in which embodiments of the present technology may be used.

FIG. 1 is an illustration of an environment in which embodiments of the present technology may be used. A user may act as an audio (speech) source 102 to an audio device 104. The exemplary audio device 104 includes two microphones: a primary microphone 106 relative to the audio source 102 (target source) and a secondary microphone 108 located a distance away from the primary microphone 106. In other embodiments, the audio device 104 may include more than two microphones, such as for example three, four, five, six, seven, eight, nine, ten or even more microphones.

The primary microphone 106 and secondary microphone 108 may be omni-directional microphones. Alternatively embodiments may utilize other forms of microphones or acoustic sensors, such as directional microphones.

While the microphones 106 and 108 receive sound (i.e. acoustic signals) from the audio source 102, the microphones 106 and 108 also pick up noise 112. Although the noise 112 is shown coming from a single location in FIG. 1, the noise 112 may include any sounds from one or more locations that differ from the location of audio source 102, and may include reverberations and echoes. The noise 112 may be stationary, non-stationary, and/or a combination of both stationary and non-stationary noise.

Some embodiments may utilize level differences (e.g. energy differences) between the acoustic signals received by the two microphones 106 and 108. Because the primary microphone 106 is much closer to the audio source 102 than the secondary microphone 108 in a close-talk use case, the intensity level is higher for the primary microphone 106, resulting in a larger energy level received by the primary microphone 106 during a speech/voice segment, for example.

Figure 2:
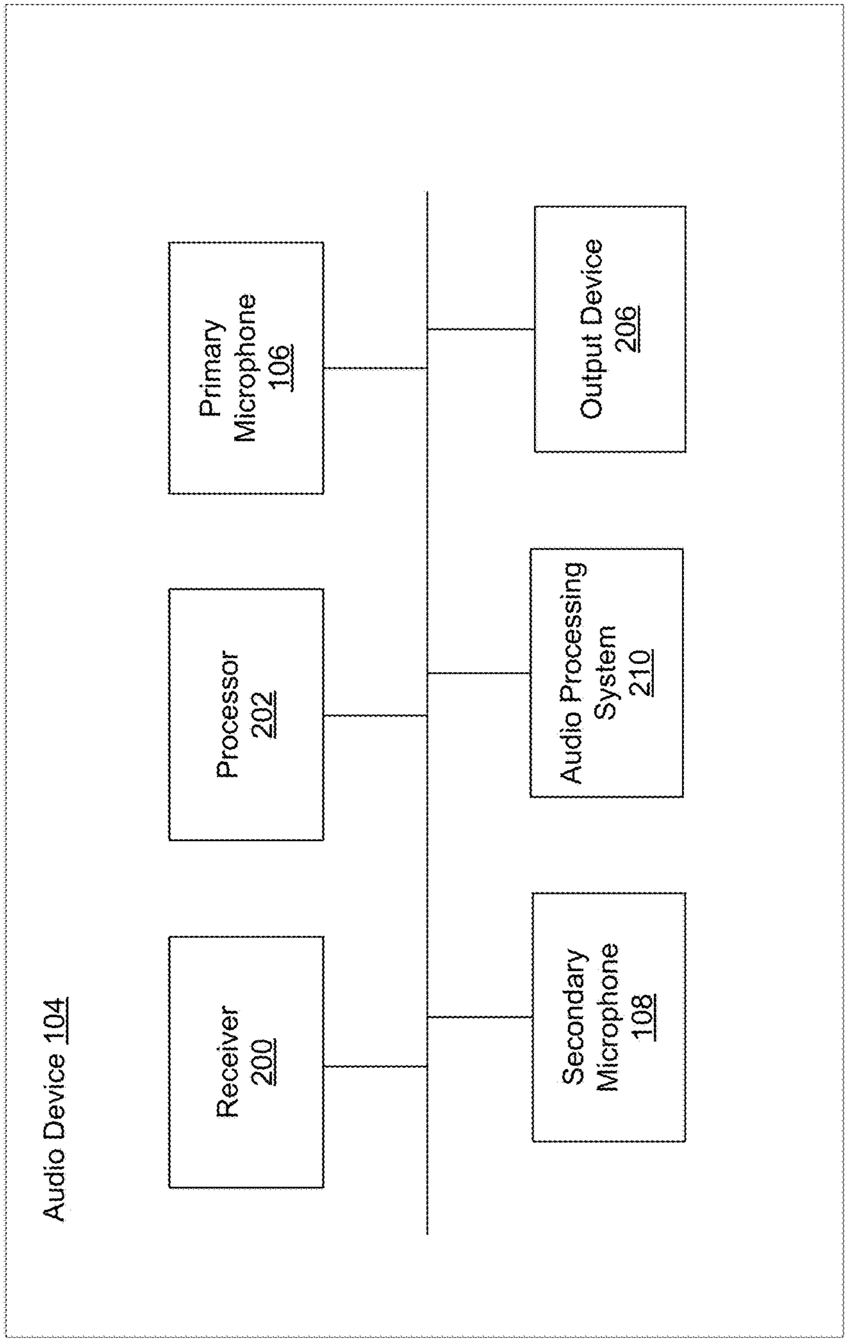
FIG. 2 is a block diagram of an exemplary audio device.

FIG. 2 is a block diagram of an exemplary audio device 104. In the illustrated embodiment, the audio device 104 includes a receiver 200, a processor 202, the primary microphone 106, an optional secondary microphone 108, an audio processing system 210, and an output device 206. The audio device 104 may include further or other components necessary for audio device 104 operations. Similarly, the audio device 104 may include fewer components that perform similar or equivalent functions to those depicted in FIG. 2.

Processor 202 may execute instructions and modules stored in a memory (such as the blocks discussed with respect to FIG. 3) in the audio device 104 to perform functionality described herein, including noise reduction for an acoustic signal. Processor 202 may include hardware and software implemented as a processing unit, which may process floating point operations and other operations for the processor 202.

The exemplary receiver 200 is an acoustic sensor configured to receive a signal from a communications network. In some embodiments, the receiver 200 may include an antenna device. The signal may then be forwarded to the audio processing system 210 to reduce noise using the techniques described herein, and provide an audio signal to the output device 206. The present technology may be used in one or both of the transmit and receive paths of the audio device 104.

The audio processing system 210 is configured to receive the acoustic signals from an acoustic source via the primary microphone 106 and secondary microphone 108 and process the acoustic signals. Processing may include performing noise reduction within an acoustic signal. The audio processing system 210 is discussed in more detail below. The primary and secondary microphones 106, 108 may be spaced a distance apart in order to allow for detecting an energy level difference, time difference or phase difference between them. The acoustic signals received by primary microphone 106 and secondary microphone 108 may be converted into electrical signals (i.e. a primary electrical signal and a secondary electrical signal). The electrical signals may themselves be converted by an analog-to-digital converter (not shown) into digital signals for processing in accordance with some embodiments. In order to differentiate the acoustic signals for clarity purposes, the acoustic signal received by the primary microphone 106 is herein referred to as the primary acoustic signal, while the acoustic signal received from by the secondary microphone 108 is herein referred to as the secondary acoustic signal. The primary acoustic signal and the secondary acoustic signal may be processed by the audio processing system 210 to produce a signal with an improved signal-to-noise ratio.

The output device 206 is any device which provides an output such as audio output to the user. For example, the output device 206 may include a speaker, an earpiece of a headset or handset, a touch screen, or a speaker on a conference device.

In various embodiments, where the primary and secondary microphones are omni-directional microphones that are closely-spaced (e.g., 1-2 cm apart), a beamforming technique may be used to simulate forwards-facing and backwards-facing directional microphones. The level difference may be used to discriminate speech and noise in the time-frequency domain which can be used in noise reduction.

Figure 3:
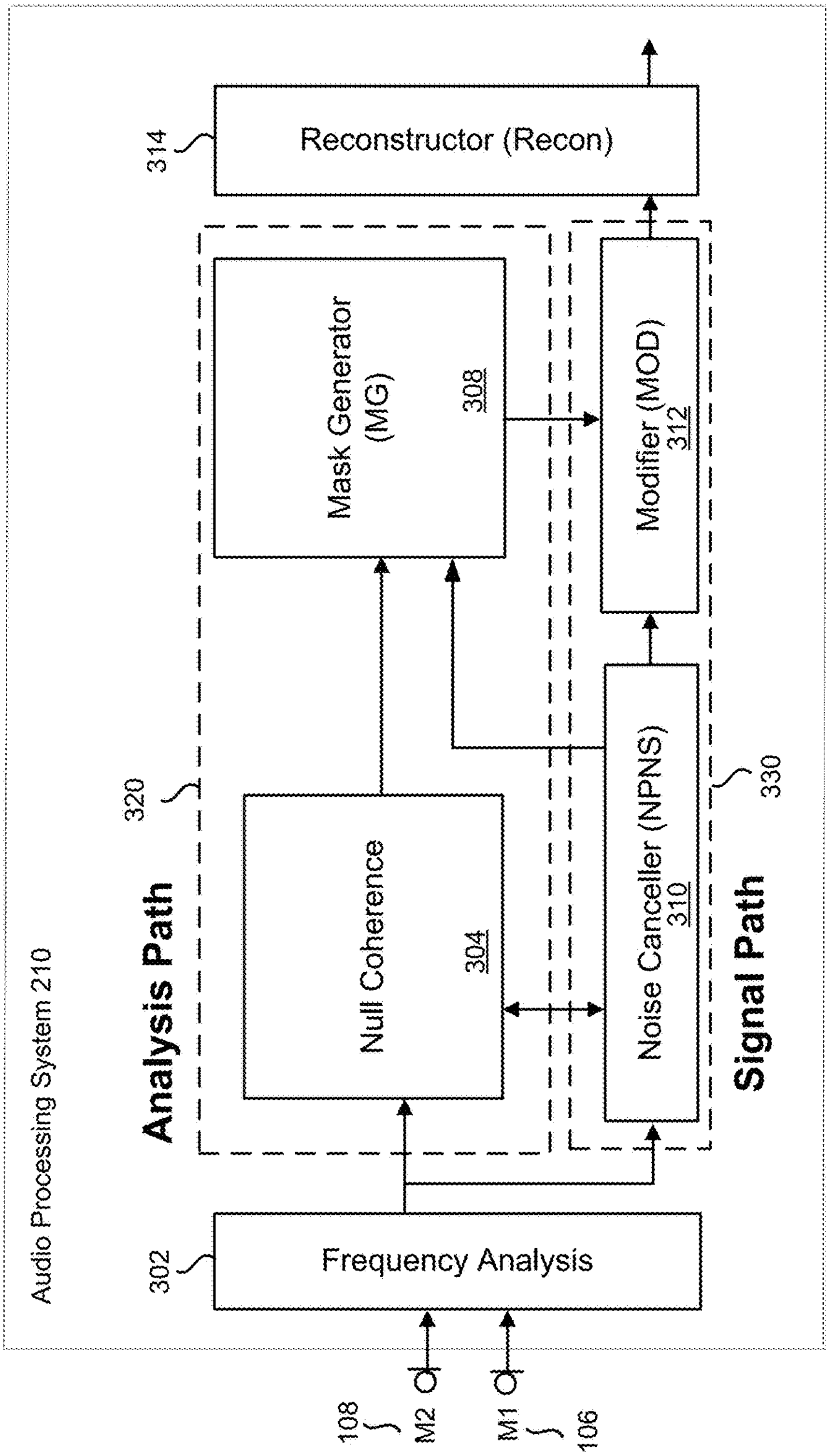
FIG. 3 is a block diagram of an exemplary audio processing system.

FIG. 3 is a block diagram of an exemplary audio processing system 210 for performing noise reduction as described herein. In exemplary embodiments, the audio processing system 210 is embodied within a memory device within audio device 104. The audio processing system 210 may include a frequency analysis module 302, null coherence module 304, mask generator module 308, noise canceller module 310, modifier module 312, and reconstructor module 314. Audio processing system 210 may include more or fewer components than illustrated in FIG. 3, and the functionality of modules may be combined or expanded into fewer or additional modules. Exemplary lines of communication are illustrated between various modules of FIG. 3, and in other figures herein. The lines of communication are not intended to limit which modules are communicatively coupled with others, nor are they intended to limit the number of and type of signals communicated between modules.

In operation, acoustic signals received from the primary microphone 106 and secondary microphone 108 are converted to electrical signals, and the electrical signals are processed through frequency analysis module 302. The acoustic signals may be pre-processed in the time domain before being processed by frequency analysis module 302. Time domain pre-processing may include applying input limiter gains, speech time stretching, and filtering using a finite impulse response (FIR) or infinite impulse response (IIR) filter.

The frequency analysis module 302 takes the acoustic signals and mimics the frequency analysis of the cochlea (e.g., cochlear domain), simulated by a filter bank. The frequency analysis module 302 separates each of the primary and secondary acoustic signals into two or more frequency sub-band signals. A sub-band signal is the result of a filtering operation on an input signal, where the bandwidth of the filter is narrower than the bandwidth of the signal received by the frequency analysis module 302. The filter bank may be implemented by a series of cascaded, complex-valued, first-order IIR filters. Alternatively, other filters such as short-time Fourier transform (STFT), sub-band filter banks, modulated complex lapped transforms, cochlear models, wavelets, etc., can be used for the frequency analysis and synthesis. The samples of the frequency sub-band signals may be grouped sequentially into time frames (e.g. over a predetermined period of time). For example, the length of a frame may be 4 ms, 8 ms, or some other length of time. In some embodiments there may be no frame at all. The results may include sub-band signals in a fast cochlea transform (FCT) domain.

The sub-band frame signals are provided from frequency analysis module 302 to an analysis path sub-system 320 and a signal path sub-system 330. The analysis path sub-system 320 may process the signal to identify signal features, distinguish between speech components and noise components of the sub-band signals, and generate a signal modifier. The signal path sub-system 330 is responsible for modifying sub-band signals of the primary acoustic signal by reducing noise in the sub-band signals. Noise reduction can include applying a modifier, such as a multiplicative gain mask generated in the analysis path sub-system 320, or subtracting components from the sub-band signals. The noise reduction may reduce noise and preserve the desired speech components in the sub-band signals.

Signal path sub-system 330 includes noise canceller module 310 and modifier module 312. Noise canceller module 310 receives sub-band frame signals from frequency analysis module 302. Noise canceller module 310 may subtract (e.g., cancel) a noise component from one or more sub-band signals of the primary acoustic signal. As such, noise canceller module 310 may output sub-band estimates of noise components in the primary signal and sub-band estimates of speech components in the form of noise-subtracted sub-band signals.

Noise canceller module 310 may provide noise cancellation, for example in systems with two-microphone configurations, based on source location by means of a subtractive algorithm. Noise canceller module 310 may also provide echo cancellation and is intrinsically robust to loudspeaker and Rx path non-linearity. By performing noise and echo cancellation (e.g., subtracting components from a primary signal sub-band) with little or no voice quality degradation, noise canceller module 310 may increase the signal-to-noise ratio (SNR) in sub-band signals received from frequency analysis module 302 and provided to modifier module 312 and post filtering modules. The amount of noise cancellation performed may depend on the diffuseness of the noise source and the distance between microphones, both of which contribute towards the coherence of the noise between the microphones, with greater coherence resulting in better cancellation.

Noise canceller module 310 may be implemented in a variety of ways. In some embodiments, noise canceller module 310 may be implemented with a single null processing noise subtraction (NPNS) module. Alternatively, noise canceller module 310, also referred to variously herein as noise canceller (NPNS) module 310 and NPNS 310, may include two or more NPNS modules, which may be arranged for example in a cascaded fashion.

An example of noise cancellation performed in some embodiments by the noise canceller module 310 is disclosed in U.S. patent application Ser. No. 12/215,980, entitled "System and Method for Providing Noise Suppression Utilizing Null Processing Noise Subtraction," filed Jun. 30, 2008, U.S. application Ser. No. 12/422,917, entitled "Adaptive Noise Cancellation," filed Apr. 13, 2009, and U.S. application Ser. No. 12/693,998, entitled "Adaptive Noise Reduction Using Level Cues," filed Jan. 26, 2010, the disclosures of which are each incorporated herein by reference.

The null coherence module 304 of the analysis path sub-system 320 receives the sub-band frame signals derived from the primary and secondary acoustic signals provided by frequency analysis module 302 as well as an output of NPNS module 310. Null coherence module 304 computes frame energy estimations of the sub-band signals and output of the noise canceller, and uses these features to generate the inter-microphone level differences (ILD), null coherence, and signal to noise ratio (SNR). The null coherence module 304 may both provide inputs to and process outputs from NPNS module 310.

The mask generator module 308 generates a multiplicative mask. The multiplicative mask is applied to the estimated noise subtracted sub-band signals provided by NPNS 310 to modifier 312. The modifier module 312 multiplies the gain masks to the noise-subtracted sub-band signals of the primary acoustic signal output by the NPNS module 310. Applying the mask reduces energy levels of noise components in the sub-band signals of the primary acoustic signal and results in noise reduction.

Mask generator 308 may generate a mask based on features in signals received by audio processing system 210. In some embodiments, mask generator 308 may receive information from which the mask is generated from noise canceller 310. For example, when noise in the received primary acoustic signal and secondary acoustic signal is not diffuse, a noise suppression mask for reducing noise by modifier 312 may be derived by an estimated compensation factor. The estimated compensation may be generated from the adaptation of a null signal, where the adaptation is controlled by a blocking matrix provided by a noise cancellation module. The blocking matrix may be generated by noise canceller module 310 and provided to mask generator 308.

The multiplicative mask may be defined by a Wiener filter and a voice quality optimized suppression system. The Wiener filter estimate may be based on the power spectral density of noise and a power spectral density of the primary acoustic signal. The Wiener filter derives a gain based on the noise estimate. The derived gain is used to generate an estimate of the theoretical minimum mean square error (MMSE) of the clean speech signal given the noisy signal. To limit the amount of speech distortion as a result of the mask application, the Wiener gain may be limited at a lower end using a perceptually-derived gain lower bound.

The values of the gain mask output from mask generator module 308 are time and sub-band signal dependent and optimize noise reduction on a per sub-band basis. The noise reduction may be subject to the constraint that the speech loss distortion complies with a tolerable threshold limit.

In some embodiments, the energy level of the noise component in the sub-band signal may be reduced to no less than a residual noise target level, which may be fixed or slowly time-varying. In some embodiments, the residual noise target level is the same for each sub-band signal, in other embodiments it may vary across sub-bands. Such a target level may be a level at which the noise component ceases to be audible or perceptible, below a self-noise level of a microphone used to capture the primary acoustic signal, or below a noise gate of a component on a baseband chip or of an internal noise gate within a system implementing the noise reduction techniques.

Modifier module 312 receives the signal path cochlear samples from noise canceller module 310 and applies a gain mask received from mask generator 308 to the received samples. The signal path cochlear samples may include the noise subtracted sub-band signals for the primary acoustic signal. The mask provided by the Wiener filter estimation may vary quickly, such as from frame to frame, and noise and speech estimates may vary between frames. To help address the variance, the upwards and downwards temporal slew rates of the mask may be constrained to within reasonable limits by modifier 312. The mask may be interpolated from the frame rate to the sample rate using simple linear interpolation, and applied to the sub-band signals by multiplicative noise suppression. Modifier module 312 may output masked frequency sub-band signals.

Reconstructor module 314 may convert the masked frequency sub-band signals from the cochlea domain back into the time domain. The conversion may include adding the masked frequency sub-band signals and phase shifted signals. Alternatively, the conversion may include multiplying the masked frequency sub-band signals with an inverse frequency of the cochlea channels. Once conversion to the time domain is completed, the synthesized acoustic signal may be output to the user via output device 206 and/or provided to a codec for encoding.

In some embodiments, additional post-processing of the synthesized time domain acoustic signal may be performed. For example, comfort noise generated by a comfort noise generator may be added to the synthesized acoustic signal prior to providing the signal to the user. Comfort noise may be a uniform constant noise that is not usually discernible to a listener (e.g., pink noise). This comfort noise may be added to the synthesized acoustic signal to enforce a threshold of audibility and to mask low-level non-stationary output noise components. In some embodiments, the comfort noise level may be chosen to be just above a threshold of audibility and may be settable by a user. In some embodiments, the mask generator module 308 may have access to the level of comfort noise in order to generate gain masks that will suppress the noise to a level at or below the comfort noise.

The system of FIG. 3 may process several types of signals received by an audio device. The system may be applied to acoustic signals received via one or more microphones. The system may also process signals, such as a digital Rx signal, received through an antenna or other connection.

Figure 4:
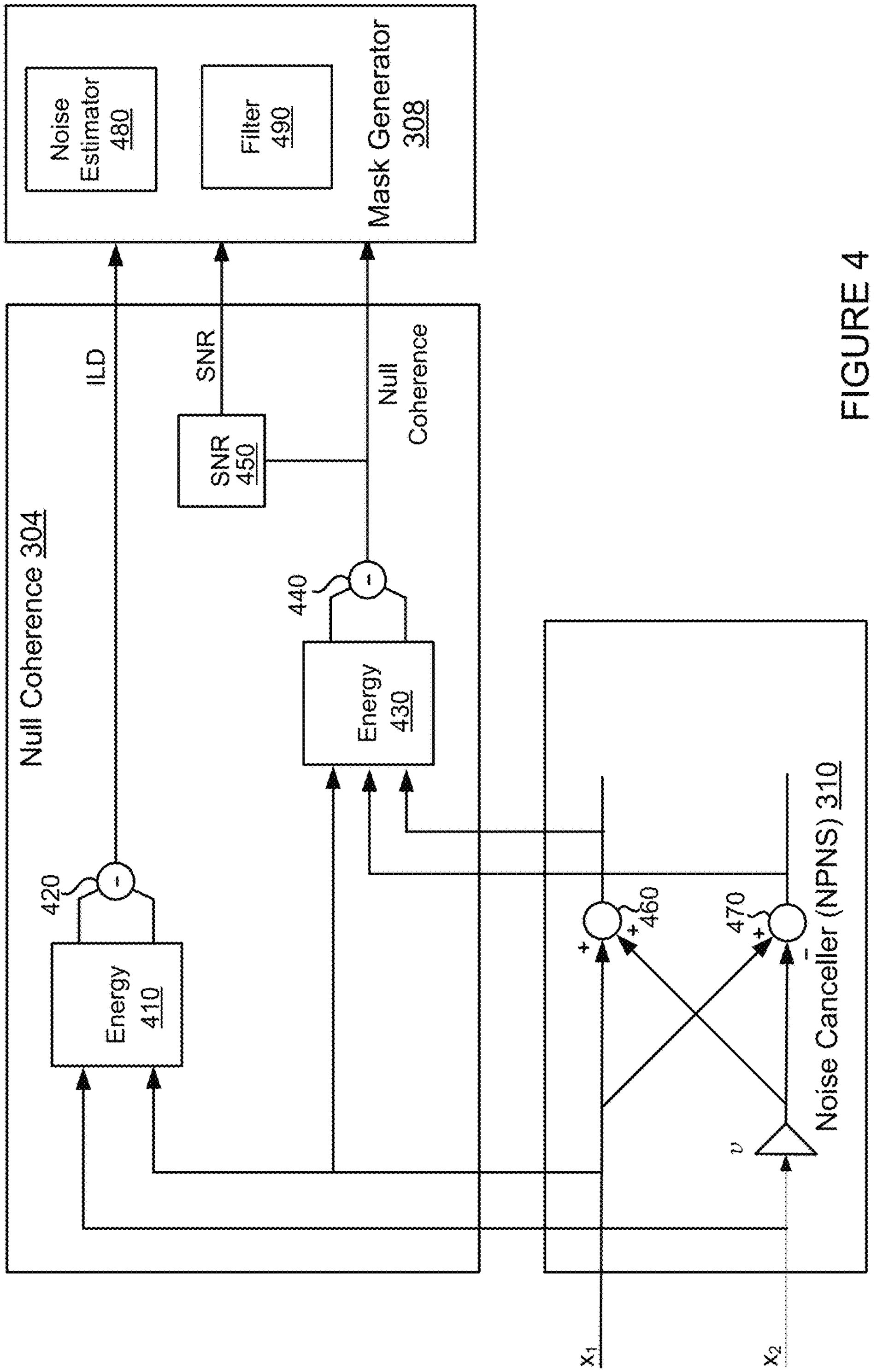
FIG. 4 is a block diagram of an exemplary null coherence processor.

FIG. 4 is a block diagram of an exemplary null coherence processor. The null processor of FIG. 4 may provide more detail for audio processing system 210 of the system of FIG. 3. Null coherence module 304 of FIG. 4 includes energy module 410, combiner module 420, energy module 430, combiner module 440, and SNR module 450. FIG. 4 also illustrates, in addition to the audio processing system 210, noise canceller 310 and mask generator 308.

Null coherence module 304 may generate an ILD for one or more sub-bands within a particular frame. The sub-band signals are received by energy module 410, which provides energy levels for the signals to combiner 420. The energy signals from energy module 410 are then provided to combiner 420. Combiner 420 may provide an ILD for the primary microphone and secondary microphone signals as a ration of the energy signals from the microphones. The ILD may be represented mathematically by $$ILD = \left\lceil \left\lfloor c \cdot \log_2\left(\frac{E_1}{E_2}\right) \right\rfloor_{-1} \right\rceil_{+1}$$

where E1 and E2 are the energy outputs of the primary and secondary microphones 106, 108, respectively, computed in each sub-band signal over non-overlapping time intervals ("frames"). This equation describes the dB ILD normalized by a factor of c and limited to the range [−1, +1]. Thus, when the audio source 102 is close to the primary microphone 106 for E1 and there is no noise, ILD=1, but as more noise is added, the ILD will be reduced.

Determining energy level estimates and inter-microphone level differences is discussed in more detail in U.S. patent application Ser. No. 11/343,524, entitled "System and Method for Utilizing Inter-Microphone Level Differences for Speech Enhancement", and U.S. patent application Ser. No. 12/832,920, filed Jul. 8, 2010, titled "Multi-Microphone Robust Noise Suppression," the disclosures of which are incorporated by reference herein.

Null coherence module 304 may generate a null coherence from a null processed signal received from noise canceller 310. Null coherence module may receive null processed signals from noise canceller 310, for example from a first stage of a multi-stage noise canceller module which ultimately removes noise from a primary acoustic signal received from a primary microphone. A first received signal may be represented as $x_1+\upsilon x_2$, generated as an output of combiner 460 in noise canceller 310 in FIG. 4, wherein $\upsilon$ may be a complex coefficient that nullifies the target source in the primary signal. A second signal received by null coherence module 304 may be a null processed signal represented as $x_1-\upsilon x_2$, generated as an output of combiner 470 in noise canceller 310 in FIG. 4. The output of combiner 470 may include a blocking matrix signal.

Energy module 430 receives the first signal and second signal as well as the primary microphone signal $x_1$ and may provide energy values for each signal. Combiner 440 receives two of the energy signals from energy module 430 and provides an energy ratio between the two signals. The signals can be expressed as $x_1=s+n_1$ and $x_{2=1}/\upsilon s+n_2$ where s is the speech signal, $n_1$ is the noise at the primary microphone, $n_2$ is the noise at the secondary microphone, and $\upsilon$ can be viewed as representing the transfer function between the primary and the secondary microphone. The energy ratio provided by combiner 440 may be represented as:

$$G_1 = \frac{E\{(x_1)\}^2}{E\{(x_1 - vx_2)^2\}} = \frac{P_s + P_n}{(1 + |v|^2)P_n}$$

wherein $G_1$ represents the null coherence for the sub-band and frame and is the ratio of the energy of the primary microphone and the energy of the null output of the noise canceller. $P_s$ and $P_n$ represent the energy of the clean speech and of the noise, respectively and it is assumed that the noise energy is identical at both microphones. The null coherence is the portion of a signal that has high coherence and can be nullified by a null processor, such as noise canceller 310. When the desired speech source is present in the sub-band microphone signals, the ratio G is high, the coherence is high. A low value for G indicates a low coherence and an absence of the speech source.

The energy ratio provided by combiner 440 may also be represented as:

$$G_2 = \frac{E\{(x_1 + vx_2)^2\}}{E\{(x_1 - vx_2)^2\}} = \frac{4P_s + (1 + |v|^2)P_n}{(1 + |v|^2)P_n},$$

wherein $G_2$ is the ratio of the energy of both the primary and secondary microphone signals and the energy of the null output of the noise canceller. The ratio $G_2$ represents the null coherence for the sub-bands and may be used to reduce the effect of microphone mismatch.

The mask generator 308 may generate a mask based on the null coherence and ILD. When null coherence is high (i.e., near one) for a sub-band, the present technology may presume that the sub-band is dominated by speech and the noise estimate for that sub-band is frozen. When the null coherence for a sub-band is low (i.e., near zero), the noise estimate for the sub-band may be set equal to the noise canceller output signal energy for that sub-band. The mask generator generates a mask to apply against each sub-band for the current band and provides the mask to modifier module 312.

In some embodiments, mask generator module may use ILD as an additional cue for identifying speech in a sub-band. For example, when both the null coherence and an ILD are high or low for a particular sub-band, the mask generator may generate a mask as discussed above based on the null coherence value. If a null coherence is high and an ILD is low, or vice versa, the mask generator may generate a mask having less than the energy value of the output of the noise canceller.

In some embodiments, null coherence module may generate an SNR value as a cue for determining whether a sub-band is dominated by noise or speech. When noise is diffuse and the microphones are far apart from each other, the energy of the noise in the primary signal may be equal to the energy of the noise in the secondary acoustic signal, and the energy. This may be represented as:

$$E\{(n_1)^2\} = E\{(n_2)^2\} = P_n$$

$$E\{(n_1 n_2^*)\} = 0$$

Typically, $G_2$ may be used as a cue for noise suppression in close-talk situations where the target speech is present mostly in the primary signal $x_1$. In far-talk situations where the two microphones play a more symmetrical role, $G_1$ may be used as a cue for performing noise suppression. $G_1$ may be a function of the SNR which can be used in conjunction with the ILD.

Null coherence module 304 computes a null signal and a delay-and-sum signal from the primary acoustic signal and secondary acoustic signal, corresponding to primary and secondary microphones respectively. If is the null coefficient that maps the secondary microphone to the primary microphone the null signal is computed as:

$$A_{null}=A_{pri}-{}^*A_{sec}$$

and the delay-and-sum signal as $$Adas=A_{pri}+{}^*A_{sec}.$$

The delay-and-sum signal may be used in a far-talk mode (for example, where the speech source is positioned away from the microphones). In a close-talk mode, the primary input signal may be used instead. In some embodiments, the current implementation may use the primary signal for both modes.

Mask generator 308 may include a Noise Estimator 480 and Filter module 490. With the energy information from the null coherence module, Mask Generator 308 may estimate a multiplicative mask.

Noise Estimator 480 may receive the energies from the NP module, $E_{null}$ and $E_{das}$, and the primary microphone $E_{pri}$ to derive an estimate of the null-incoherent component in the input signals. In some embodiments, this is performed when the microphones are sufficiently separated and the coherence function for the diffuse field is sufficiently low for all frequencies of interest.

In some embodiments, when the diffuseness assumptions are not sufficiently low, the compensation factor that translates the null signal into a noise estimate at the primary microphone is no longer $(1+v^2)$ and may be estimated. Hence, an adaptive system may be implemented via temporal filters, a gain module, or in some other manner.

In some embodiments, the null signal from Null Coherence 304 may be converted to the logarithmic domain and provided to Filter module 490 for estimating the coefficients of the temporal filters. A temporal filter may be applied independently to each tap, and may consist of a FIR filter adapted using the normalized least mean square (NLMS) algorithm. These filters may be adapted relatively slowly to attempt to learn the changes in the compensation function. The filtered output is then converted back to the linear domain via an exp function and may be used to derive the multiplicative mask.

The adaptation of the temporal filters may be controlled by an alpha adaptation control VAD from noise canceller 310 and the primary input signal used as desired target during non-speech segments. A slow adaptation may be implemented during speech segments to prevent divergence of the filter coefficients to the speech signal.

The mask computation may be based on selecting components having an energy level that is above an energy level of a detected noise floor and which have a large coherent-to-incoherent ratio. This ratio may be computed by dividing the primary microphone energy by the compensated noise estimate energy. This ratio is may be tracked using a percentile tracker. A threshold may be selected based on the percentile tracker to decide if the segment corresponds to the target speech.

Figure 5:
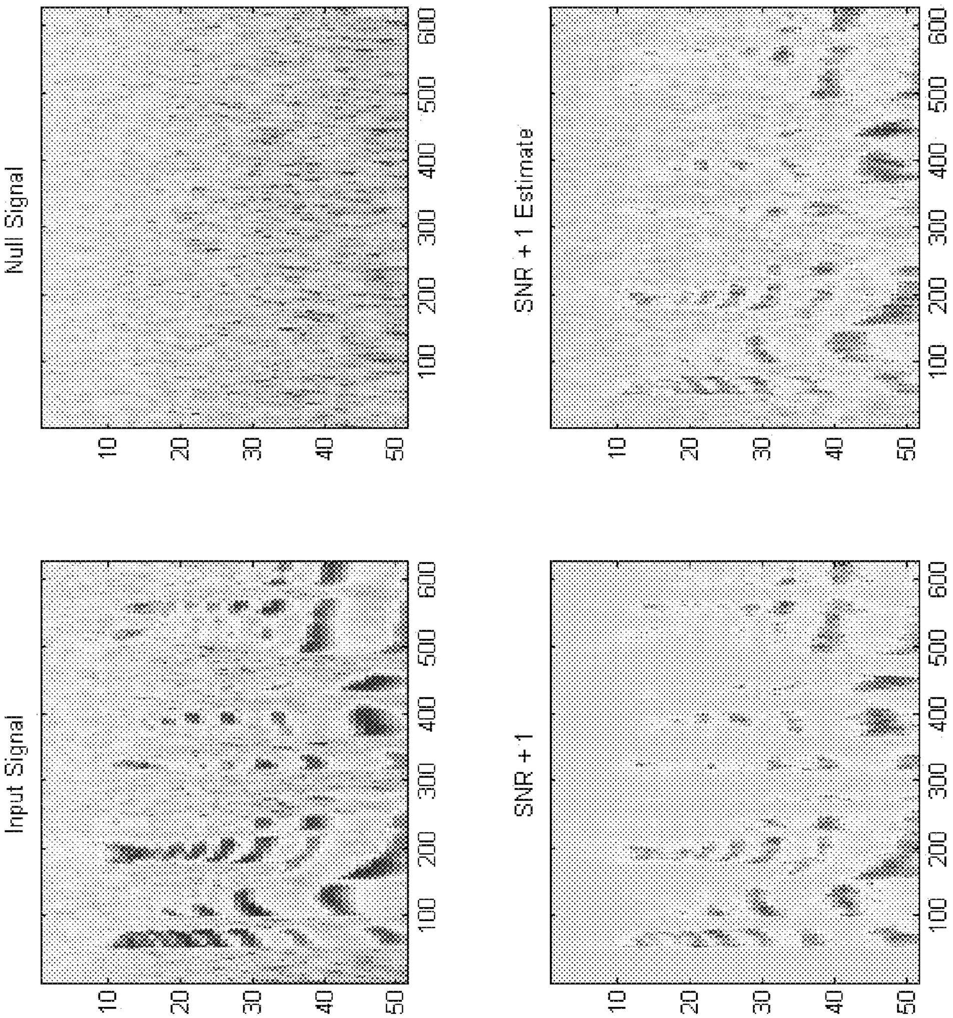
FIG. 5 is an illustration of SNR estimates derived from null coherence.

FIG. 5 is an illustration of SNR estimates derived from null coherence. For example, as illustrated in FIG. 5, a speech signal corrupted by diffuse pink noise is shown, together with the null signal and the SNR estimate derived from the ratio $G_1$ as follows:

The SNR may be expressed as a function of $G_1$ by:

$$SNR=G_1(1+|v|^2)-1.$$

Using the definition of $G_2$ above, the SNR may also be represented as:

$$SNR = (G_2 - 1)\frac{1+|v|^2}{4}.$$

The SNR for the particular sub-band may be used as an additional cue to determine if the presently considered sub-band is dominated by noise or desired speech.

Figure 6:
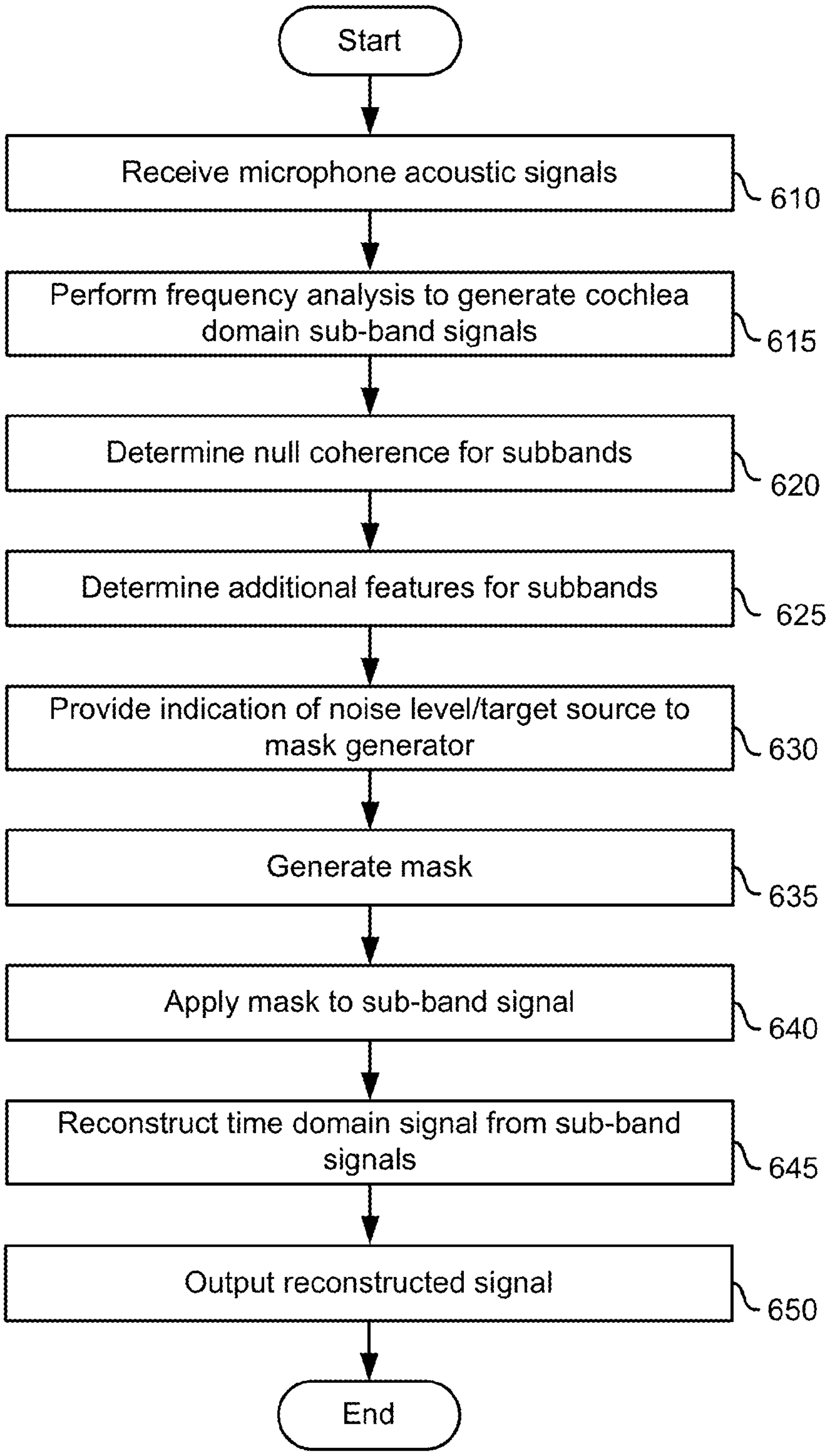
FIG. 6 is a flowchart of an exemplary method for performing noise reduction based on null coherence.

FIG. 6 is a flowchart of an exemplary method for performing noise reduction based on null coherence. Microphone acoustic signals may be received at step 610. The acoustic signals received by microphones 106 and 108 may each include at least a portion of speech and noise. Frequency analysis is performed on the received sub-band signals to generate cochlea domain signals at step 615. The sub-band signals may be generated from time domain signals using a cascade of complex filters. In some embodiments, pre-processing may be performed on the acoustic signals before generating sub-band signals. The pre-processing may include applying a gain, equalization and other signal processing to the acoustic signals.

Null coherence is determined for the sub-bands at step 620. The null coherence may be based on features extracted from the sub-band signals. Performing null coherence is discussed in more detail with respect to FIG. 7.

Additional features may be determined for the sub-bands at step 625. The additional features may include ILD, SNR and other features for the sub-bands signals. The ILD may be generated as a ratio between the energies of the primary microphone signal and the secondary microphone signal. The SNR may be determined from the null coherence under certain conditions, for example when noise is diffuse.

An indication of the noise level and target source is provided to mask generator 308 at step 630. The indication may be based on the null coherence determined at step 620. When null coherence is low, the indicator may communicate that the current sub-band is dominated by noise. When the null coherence is high, the indicator may communicate that the sub-band is dominated by a target source. In some embodiments, the indication may also be based at least in part on an ILD and/or SNR. For example, an indication that a current sub-band is dominated by noise may be based on both a low null coherence and low SNR. Similarly, an indication that the current sub-band is dominated by a target source may be based on both a high null coherence and a high (i.e., near a value of one) ILD.

A mask is generated at step 635. The mask may be generated by mask generator 308 based on the indication received from null coherence module 304. A mask may be generated and applied to each sub-band during each frame based on a determination as to whether the particular sub-band is determined to be noise or a target source (i.e., speech). In some embodiments, the mask may be created to suppress the sub-band energy in the current frame if the received suggest the current sub-band is noise. The mask may not suppress any energy if the indication suggests the sub-band energy in the current sub-band is dominated by a target source of speech. In some embodiments, the mask may be generated by based on a level of suppression determined from one or more of the null coherence, ILD and SNR.

The mask may then be applied to a sub-band at step 640. The mask may be applied by modifier 312 to the sub-band signals output by noise canceller 310. The mask may be interpolated from frame rate to sample rate by modifier 312.

A time domain signal is reconstructed from sub-band signals at step 645. The time band signal may be reconstructed by applying a series of delays and complex multiply operations to the sub-band signals by reconstructor module 314. In some embodiments, post processing may be performed on the reconstructed time domain signal. The post processing may be performed by a post processor and may include applying an output limiter to the reconstructed signal, applying an automatic gain control, and other post-processing. The reconstructed output signal may then be output at step 650.

Figure 7:
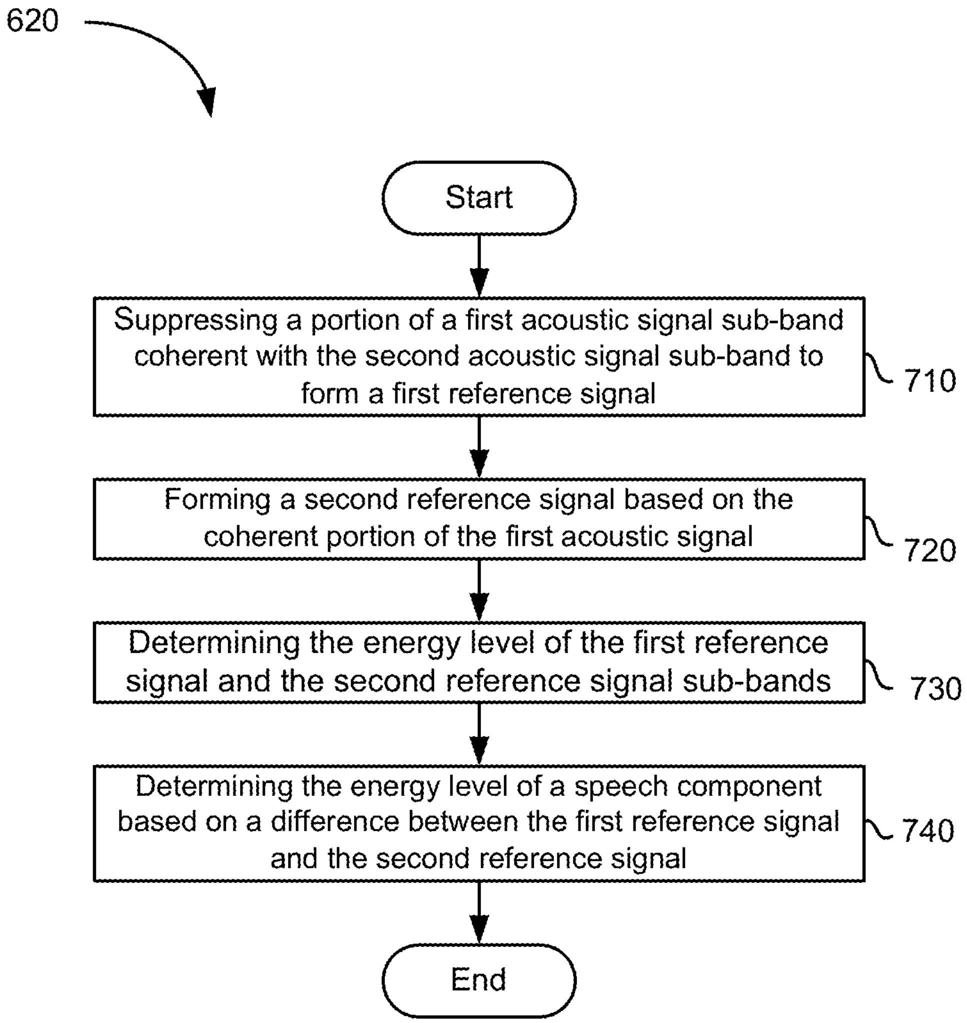
FIG. 7 is a flowchart of an exemplary method for determining null coherence.

FIG. 7 is a flowchart of an exemplary method for determining null coherence for sub-bands. The method of FIG. 7 may provide more detail for step 620 of the method of FIG. 6. A portion of a first acoustic signal sub-band coherent with the second acoustic signal sub-band is suppressed to form a first reference signal at step 710. The first reference signal may be generated in noise canceller 310. A second reference signal may be formed based on the coherent portion of the first acoustic signal at step 720. The second reference signal may also be generated in noise canceller 310.

The energy level of the first reference signal and the second reference signal sub-bands may be determined at step 730. The energy levels may be determined by energy module 430 which receives the reference signals from noise canceller 310. The energy level of the speech component is determined from a difference between the first reference signal and the second reference signal at step 740.

The above described modules, including those discussed with respect to FIG. 3, may include instructions stored in a storage media such as a machine readable medium (e.g., computer readable medium). These instructions may be retrieved and executed by the processor 202 to perform the functionality discussed herein. Some examples of instructions include software, program code, and firmware. Some examples of storage media include memory devices and integrated circuits.

While the present invention is disclosed by reference to the preferred embodiments and examples detailed above, it is to be understood that these examples are intended in an illustrative rather than a limiting sense. It is contemplated that modifications and combinations will readily occur to those skilled in the art, which modifications and combinations will be within the spirit of the invention and the scope of the following claims.

What is claimed is:

1. A method for reducing noise within an acoustic signal, the method comprising:

receiving a first acoustic signal and a second acoustic signal;

determining an energy level of a noise component in the first acoustic signal based on a spatial null in a desired direction and a coherence between the first and second acoustic signals; and applying a signal modification to the first acoustic signal to reduce the energy level of the noise component, the signal modification based on the determined energy level of the noise component.

2. The method of claim 1, wherein the coherence is a measurement between the first acoustic signal and an output of a spatial processor.

3. The method of claim 2, further comprising determining a signal to noise ratio between the first acoustic signal and the output of the spatial processor.

4. The method of claim 3, wherein null coherence is a ratio of the energy level of the first acoustic signal and the energy level of a null signal.

5. The method of claim 3, wherein null coherence is a ratio of the energy level of the combination of the first acoustic signal and the second acoustic signal and the energy level of the output of a null processor.

6. The method of claim 1, further comprising separating the first acoustic signal into a plurality of first acoustic sub-band signals and separating the second acoustic signal into a plurality of second acoustic sub-band signals, and wherein determining the energy level of the noise component and applying the signal modification are on a per sub-band signal basis for the first and second plurality of acoustic sub-band signals.

7. The method of claim 1, wherein determining the energy level of the noise component in the first acoustic signal is further based on an energy level difference between the first and second acoustic signals.

8. The method of claim 1, wherein the signal modification is determined at least in part based on an inter-microphone level difference between the first acoustic signal and the second acoustic signal.

9. The method of claim 1, further comprising:

determining a signal to noise ratio based on the null coherence; and determining the signal modification at least in part on the signal to noise ratio.

10. A non-transitory computer readable storage medium having embodied thereon a program, the program being executable by a processor to perform a method for processing an audio signal, the method comprising:

receiving a first acoustic signal and a second acoustic signal;

determining an energy level of a noise component in the first acoustic signal based on a spatial null in a desired direction and a coherence between the first and second acoustic signals;

and applying a signal modification to the first acoustic signal to reduce the energy level of the noise component, the signal modification based on the determined energy level of the noise component.

11. The non-transitory computer readable storage medium of claim 10, wherein the coherence is a measurement between the first acoustic signal and an output of a null coherence module.

12. The non-transitory computer readable storage medium of claim 11, further comprising determining a signal to noise ratio between the first acoustic signal and the output of the null coherence module.

13. The non-transitory computer readable storage medium of claim 12, wherein null coherence is a ratio of the energy level of the first acoustic signal and the energy level of a null signal.

14. The non-transitory computer readable storage medium of claim 12, wherein null coherence is a ratio of the energy level of the combination of the first reference signal and the second reference signal and the energy level of the combination of the first and second acoustic signals.

15. The non-transitory computer readable storage medium of claim 10, the method further comprising separating the first acoustic signal into a plurality of first acoustic sub-band signals and separating the second acoustic signal into a plurality of second acoustic sub-band signals, and wherein determining the energy level of the noise component and applying the signal modification are on a per sub-band signal basis for the first and second plurality of acoustic sub-band signals.

16. The non-transitory computer readable storage medium of claim 10, wherein determining the energy level of the noise component in the first acoustic signal is further based on an energy level difference between the first and second acoustic signals.

17. The non-transitory computer readable storage medium of claim 10, wherein the signal modification is determined at least in part based on an inter-microphone level difference between the first acoustic signal and the second acoustic signal.

18. The non-transitory computer readable storage medium of claim 10, the method further comprising:

determining a signal to noise ratio based on the null coherence; and determining the signal modification at least in part on the signal to noise ratio.

* * * * *